United States Patent
Weiner et al.

(10) Patent No.: US 9,353,035 B2
(45) Date of Patent: May 31, 2016

(54) PROCESS FOR PRODUCING ETHANOL WITH ZONAL CATALYSTS

(71) Applicant: Celanese International Corporation, Irving, TX (US)

(72) Inventors: Heiko Weiner, Pasadena, TX (US); Zhenhua Zhou, Houston, TX (US); Victor J. Johnson, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/697,371

(22) Filed: Apr. 27, 2015

(65) Prior Publication Data

US 2015/0307422 A1 Oct. 29, 2015

Related U.S. Application Data

(63) Continuation-in-part of application No. 14/263,332, filed on Apr. 28, 2014, now Pat. No. 9,024,088, and a continuation-in-part of application No. 14/263,422, filed on Apr. 28, 2014, now Pat. No. 9,073,815, and a continuation-in-part of application No. 14/263,450, filed on Apr. 28, 2014.

(51) Int. Cl.
| | |
|---|---|
| *C07C 29/149* | (2006.01) |
| *B01J 23/00* | (2006.01) |
| *B01J 23/835* | (2006.01) |
| *B01J 23/89* | (2006.01) |
| *B01J 37/00* | (2006.01) |

(52) U.S. Cl.
CPC ............... *C07C 29/149* (2013.01); *B01J 23/00* (2013.01); *B01J 23/002* (2013.01); *B01J 23/835* (2013.01); *B01J 23/8966* (2013.01); *B01J 23/8973* (2013.01); *B01J 23/8993* (2013.01); *B01J 37/0009* (2013.01); *Y02P 20/582* (2015.11)

(58) Field of Classification Search
CPC .................................................... C07C 29/149
USPC .......................................... 568/885, 913, 918
See application file for complete search history.

(56) References Cited

U.S. PATENT DOCUMENTS

| | | | |
|---|---|---|---|
| 4,398,039 A | 8/1983 | Pesa et al. | |
| 4,517,391 A | 5/1985 | Schuster et al. | |
| 4,613,700 A | 9/1986 | Maki et al. | |
| 4,777,303 A | 10/1988 | Kitson et al. | |
| 4,804,791 A | 2/1989 | Kitson et al. | |
| 4,918,248 A | 4/1990 | Hattori et al. | |
| 5,149,680 A | 9/1992 | Kitson et al. | |
| 5,306,845 A | 4/1994 | Yokohama et al. | |
| 6,204,417 B1 | 3/2001 | Fischer et al. | |
| 6,495,730 B1 | 12/2002 | Konishi et al. | |
| 6,509,180 B1 | 1/2003 | Verser et al. | |
| 6,521,565 B1 | 2/2003 | Clavenna et al. | |
| 7,608,744 B1 | 10/2009 | Johnston et al. | |
| 7,851,404 B2 | 12/2010 | Lok | |
| 7,863,489 B2 | 1/2011 | Johnston et al. | |
| 7,884,253 B2 | 2/2011 | Stites et al. | |
| 7,923,405 B2 | 4/2011 | Kharas et al. | |
| 8,017,544 B2 | 9/2011 | Casci et al. | |
| 8,211,821 B2 | 7/2012 | Weiner et al. | |
| 8,309,772 B2 | 11/2012 | Weiner et al. | |
| 8,329,961 B2 | 12/2012 | Danjo et al. | |
| 8,455,702 B1 | 6/2013 | Zhou et al. | |
| 8,471,075 B2 | 6/2013 | Johnston et al. | |
| 8,536,236 B2 | 9/2013 | Lok et al. | |
| 8,546,622 B2 | 10/2013 | Jevtic et al. | |
| 8,680,321 B2 | 3/2014 | Johnston et al. | |
| 9,024,088 B1 | 5/2015 | Weiner et al. | |
| 9,073,815 B1 | 7/2015 | Weiner et al. | |
| 2009/0088317 A1 | 4/2009 | Frye, Jr. et al. | |
| 2011/0060169 A1 | 3/2011 | Kaizik et al. | |
| 2012/0157721 A1* | 6/2012 | Weiner | C07C 29/141 568/885 |
| 2012/0238785 A1 | 9/2012 | Zhou et al. | |
| 2013/0178661 A1 | 7/2013 | Zhou et al. | |
| 2013/0178663 A1 | 7/2013 | Zhou et al. | |
| 2013/0178664 A1 | 7/2013 | Zhou et al. | |
| 2013/0178669 A1 | 7/2013 | Zhou et al. | |
| 2013/0178670 A1 | 7/2013 | Zhou et al. | |

(Continued)

FOREIGN PATENT DOCUMENTS

| | | |
|---|---|---|
| CN | 102139234 A | 8/2011 |
| CN | 202214306 U | 5/2012 |

(Continued)

OTHER PUBLICATIONS

Castro-Grijalba, et al., "Preparation and Characterization of Catalysts Based on Cassiterite (SnO2) and it's Application in Hydrogenation of Methyl Esters", The Journal of the Argentine Chemical Society, vol. 98, 2011, pp. 48-59.

(Continued)

*Primary Examiner* — Sikarl Witherspoon
(74) *Attorney, Agent, or Firm* — Kilpatrick Townsend & Stockton LLP

(57) ABSTRACT

A process is disclosed for producing ethanol comprising contacting reactants comprising acetic acid and hydrogen in a reactor in the presence of a first catalyst in a first zone and a second catalyst in a second zone. The first catalyst is a mixed oxide comprising tin and at least one of cobalt or nickel. The second catalyst may be either: i) a supported Group VIII hydrogenation catalyst; ii) a copper-based catalyst; and iii) a secondary mixed oxide catalyst, wherein the secondary mixed oxide catalyst is different than the mixed oxide catalyst of the first zone.

19 Claims, No Drawings

(56) References Cited

U.S. PATENT DOCUMENTS

| | | |
|---|---|---|
| 2013/0225878 A1 | 8/2013 | Weiner et al. |
| 2013/0245131 A1 | 9/2013 | Zhou et al. |
| 2013/0245332 A1 | 9/2013 | Weiner et al. |
| 2013/0245338 A1 | 9/2013 | Weiner et al. |
| 2015/0307421 A1 | 10/2015 | Zhou et al. |
| 2015/0307423 A1 | 10/2015 | Weiner et al. |

FOREIGN PATENT DOCUMENTS

| | | |
|---|---|---|
| CN | 102513120 A | 6/2012 |
| CN | 102600842 A | 7/2012 |
| CN | 102658165 A | 9/2012 |
| CN | 102671682 A | 9/2012 |
| CN | 102688768 A | 9/2012 |
| CN | 102690171 A | 9/2012 |
| CN | 102757308 A | 10/2012 |
| CN | 102847535 A | 1/2013 |
| CN | 102847544 A | 1/2013 |
| CN | 102941097 A | 2/2013 |
| CN | 102941108 A | 2/2013 |
| CN | 103055956 A | 4/2013 |
| CN | 103084186 A | 5/2013 |
| CN | 103772143 A | 5/2014 |
| CN | 103785412 A | 5/2014 |
| CN | 103785414 A | 5/2014 |
| CN | 103785416 A | 5/2014 |
| CN | 103785417 A | 5/2014 |
| CN | 103785418 A | 5/2014 |
| CN | 103787827 A | 5/2014 |
| CN | 103787829 A | 5/2014 |
| CN | 103787830 A | 5/2014 |
| EP | 0 091 027 A2 | 10/1983 |
| EP | 0 175 558 A1 | 3/1986 |
| EP | 0 191 995 A1 | 8/1986 |
| JP | 2001-046874 A | 2/2001 |
| WO | 2011/094713 A1 | 8/2011 |
| WO | 2012/148509 A1 | 11/2012 |
| WO | 2012/148510 A1 | 11/2012 |
| WO | 2012/149137 A1 | 11/2012 |
| WO | 2013/054303 A1 | 4/2013 |
| WO | 2013/101756 A1 | 7/2013 |
| WO | 2013/103534 A1 | 7/2013 |

OTHER PUBLICATIONS

Non-Final Office Action mailed on Dec. 18, 2014 for U.S. Appl. No. 14/263,422, 7 pages.

Notice of Allowance mailed on Mar. 31, 2015 for U.S. Appl. No. 14/263,422, 7 pages.

Non-Final Office Action mailed on Jun. 4, 2015 for U.S. Appl. No. 14/263,450, 12 pages.

Notice of Allowance mailed on Sep. 21, 2015 for U.S. Appl. No. 14/263,450, 8 pages.

Notice of Allowance mailed on Jan. 7, 2015 for U.S. Appl. No. 14/263,332, 8 pages.

International Search Report and Written Opinion of the International Searching Authority mailed on Jul. 7, 2015 for PCT Patent Application No. PCT/US2015/027739, 10 pages.

International Search Report and Written Opinion of the International Searching Authority mailed on Jun. 29, 2015 for PCT Patent Application No. PCT/US2015/027749, 13 pages.

* cited by examiner

PROCESS FOR PRODUCING ETHANOL WITH ZONAL CATALYSTS

PRIORITY CLAIM

The present invention claims priority and is a continuation-in-part application of U.S. application Ser. Nos. 14/263,332; 14/263,422; and 14/263,450, all filed Apr. 28, 2014, the entire contents and disclosure of which are hereby incorporated by reference.

FIELD OF THE INVENTION

The present invention relates generally to processes for hydrogenating acetic acid to form ethanol with zonal catalysts that comprise at least one mixed oxide catalyst and at least one other catalyst suitable for hydrogenation.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced.

As an alternative to fermentation, ethanol may be produced by hydrogenating acetic acid and esters thereof. Ethanol production via the reduction of acetic acid generally uses a hydrogenation catalyst. The reduction of various carboxylic acids over metal oxides has been proposed.

EP0175558 describes the vapor phase formation of carboxylic acid alcohols and/or esters such as ethanol and ethyl acetate from the corresponding mono and di-functional carboxylic acid, such as acetic acid, in the presence of a copper oxide-metal oxide supported catalyst, such as $CuO/ZnAl_2O_4$. A disadvantage with copper oxide catalysts in carboxylic acid hydrogenation reactions is the lack of long-term catalyst stability.

U.S. Pat. No. 4,398,039 describes a process for the vapor phase hydrogenation of carboxylic acids to yield their corresponding alcohols in the presence of steam and a catalyst comprising the mixed oxides of ruthenium, at least one of cobalt, nickel, and optionally one of cadmium, zinc, copper, iron, rhodium, palladium, osmium, iridium and platinum. A process is further provided for the preparation of carboxylic acid esters from carboxylic acids in the absence of steam utilizing the above-identified catalysts.

U.S. Pat. No. 4,517,391 describes preparing ethanol by hydrogenating acetic acid under superatmospheric pressure and at elevated temperatures by a process wherein a predominantly cobalt-containing catalyst is used and acetic acid and hydrogen are passed through the reactor, at from 210 to 330° C., and under 10 to 350 bar, under conditions such that a liquid phase is not formed during the process. The cobalt-containing catalyst contains, as active components, from 50 to 80% by weight of Co, from 10 to 30% by weight of Cu, from 0 to 10% by weight of Mn, from 0 to 5% by weight of Mo and from 0 to 5% by weight of phosphoric acid, the percentages being based on the metal content. However, the productivity as reported in the examples of U.S. Pat. No. 4,517,391 is 89.8 grams of ethanol per kilogram of catalyst per hour, which is too low for commercial production.

U.S. Pat. No. 4,918,248 describes producing an alcohol by catalytically reducing an organic carboxylic acid ester with hydrogen in the presence of a catalyst obtained by reducing a catalyst precursor comprising (A) copper oxide and (B) titanium oxide and/or titanium hydroxide at a weight ratio of (A) to (B) in the range between 15/85 and 65/35. The component (A) may alternatively be a composite metal oxide comprising copper oxide and up to 20 wt. % of zinc oxide.

CN103785418 discloses a catalyst containing at least cobalt and tin and its application in the preparation of alcohol by carboxylic acid hydrogenation. The disclosed catalyst contains 10 wt. % to 50 wt. % cobalt and 0.1 wt. % to 50 wt. % tin in the total weight of catalyst, in addition to other metals such as silver, zinc, and zirconium. CN103785418 prepares the hydrogenation through the co-precipitation, deposition-precipitation, steamed ammonia precipitation, sol-gel, and being dissolved as alloy, then combined with one type or multiple types of suction filtration and ball milling methods.

CN103785415 discloses a method to prepare alcohol by selective hydrogenation of carboxylic acid. The disclosed catalyst contains 10 wt. % to 50 wt. % cobalt and 0.1 wt. % to 50 wt. % bismuth in the total weight of catalyst.

CN103787827 discloses a method to prepare alcohol by selective hydrogenation of carboxylic acid. The disclosed hydrogenation catalyst contains at least cobalt and a trace amount of precious metal additives of platinum, palladium or rhenium.

Some have proposed using two hydrogenation catalysts that convert either acetic acid, or ethyl acetate to ethanol in multiple beds or reactors.

U.S. Pat. No. 8,502,001 discloses processes for the conversion of ethanoic acid into ethanol by (a) introducing ethanoic acid and $H_2$ into a primary hydrogenation unit in the presence of a precious metal-based catalyst to produce ethanol and ethyl ethanoate and (b) introducing ethyl ethanoate, from step (a), together with $H_2$ into a secondary hydrogenation unit in the presence of a copper-based catalyst to produce ethanol. Ethanol from step (b) is recovered. As shown in the examples, step (a) suffers from low conversion of ethanoic acid and high selectivity to ethyl ethanoate.

U.S. Pat. No. 8,546,622 discloses a process for producing ethanol, comprising hydrogenating acetic acid in the presence of a first catalyst to form an intermediate product comprising ethanol and unreacted acetic acid; and hydrogenating the unreacted acetic acid in the present of a second catalyst to form ethanol, wherein the second catalyst comprises a first metal on an acidic support selected from the group consisting of an acidic support material selected from the group consisting of iron oxide, alumina, silica/alumina, titania, zirconia, and mixtures thereof, and a support material modified with an acidic modifier.

U.S. Pat. No. 8,704,008 discloses producing ethanol in a stacked bed reactor that comprises a first catalyst comprising platinum and tin and a second catalyst comprising copper or an oxide thereof.

US Pub. No. 2012/0157721 discloses producing ethanol in a stacked bed reactor that comprises a first catalyst and a second catalyst, wherein the first and second catalysts comprise at least one group VIII metal, and wherein the second catalyst is not a copper-based catalysts.

US Pub. No. 2012/0238785 discloses producing ethanol in a reactor that comprises a catalyst composition and a feed stream comprising acetic acid and a recycled liquid stream comprising ethyl acetate. The catalyst composition comprises a first catalyst comprising platinum, cobalt, and/or tin and a second catalyst comprising copper. The crude ethanol product may be separated and ethanol recovered.

Thus, further improvements to the hydrogenation process that incorporates stable catalysts that demonstrate high stability, conversion of acetic acid and selectivity to ethanol are needed.

SUMMARY OF THE INVENTION

In a first embodiment of the present invention, there is provided a process for producing ethanol comprising contacting reactants comprising acetic acid and hydrogen in a reactor in the presence of a first catalyst in a first zone and a second catalyst in a second zone. Together the first and second catalysts are referred to as zonal catalysts. The first catalyst comprises a mixed oxide comprising tin and at least one of cobalt or nickel. In one embodiment, the first catalyst is selected from the group consisting of: a) a binder and the mixed oxide comprises cobalt and tin, the catalyst being substantially free of rhenium, ruthenium, rhodium, palladium, osmium, iridium, platinum, and combinations thereof; b) a binder and the mixed oxide comprises a promoter metal, cobalt, and tin, wherein the promoter metal is selected from the group consisting of rhenium, ruthenium, rhodium, palladium, osmium, iridium, platinum, and combinations thereof; c) a binder, bismuth, and the mixed oxide comprises cobalt, and tin, being substantially free of rhenium, ruthenium, rhodium, palladium, osmium, iridium, platinum, and combinations thereof; d) a binder, the mixed oxide comprises cobalt and tin, and at least two promoter metals comprising ruthenium and bismuth; and e) a binder and the mixed oxide comprises nickel and tin. The second catalyst is selected from the group consisting of: i) a supported Group VIII hydrogenation catalyst; ii) a copper-based catalyst; and iii) a secondary mixed oxide catalyst, wherein the secondary mixed oxide catalyst is different than the mixed oxide catalyst of the first zone. The mixed oxide for the first catalyst may be present in an amount from 60 to 90 wt. %, based on the total weight of the first catalyst. The combined metal amount of the mixed oxide is at least 40 wt. %, based on the total weight of the first catalyst. The binder is selected from the group consisting of silica, aluminum oxide, and titania, and the binder is present in an amount from 5 to 40 wt. %, based on the total weight of the first catalyst. The second catalyst is selected from the group consisting of: i) a supported Group VIII hydrogenation catalyst; ii) a copper-based catalyst; and iii) a secondary mixed oxide catalyst, wherein the secondary mixed oxide catalyst is different than the mixed oxide catalyst of the first zone. In one embodiment, the supported Group VIII hydrogenation catalyst comprises: a) a support material selected from the group consisting of silica, silica/alumina, calcium metasilicate, pyrogenic silica, high purity silica, carbon, activated carbon, alumina, titiania, zirconia, graphite, zeolites, and mixtures thereof; b) a support modifier; c) a Group VIII metal selected from the group consisting of cobalt, rhodium, ruthenium, platinum, palladium, osmium, and iridium; and d) an active metal selected from the group consisting of rhenium, copper, iron, cobalt, vanadium, nickel, titanium, zinc, chromium, molybdenum, tungsten, tin, lanthanum, cerium, manganese, and combinations thereof. The total loading of the Group VIII metal and the active metal is from 0.01 to 25 wt. %. In one embodiment, the support modifier may comprise one or more of the following groups: a) calcium, magnesium, or potassium; b) tungsten, molybdenum, or vanadium; c) cobalt or tin. In one embodiment, the copper-based catalyst comprises from 35 to 70 wt. % copper, and zinc, chromium, or combinations thereof in an amount from 15 to 40 wt. %.

DETAILED DESCRIPTION OF THE INVENTION

The present invention relates to processes for producing ethanol by contacting reactants comprising acetic acid and hydrogen in a reactor in the presence of a first catalyst in a first zone and a second catalyst in a second zone. The first catalyst is also referred to herein as a mixed oxide catalyst. As described further herein, the mixed oxide catalyst comprises a mixed oxide comprising tin and at least one of cobalt or nickel. The second catalyst is selected from the group consisting of a supported Group VIII hydrogenation catalyst and a copper-based catalyst. Using the zonal catalysts of the present invention improves the productivity and performance of each catalyst. Each pass of reactants is contacted with two different catalysts in each of the zones to maximize the advantages of each of the different catalyst. This may allow tuning of the process by selecting combinations of catalysts to achieve improved performance. In addition, zonal catalyst may reduce the costs by reducing the need to use high loadings of expensive catalysts. In particular using mixed oxide catalysts in combination with a second catalyst may significantly reduce the need for more expensive hydrogenation catalysts.

Zonal Catalysts

The zonal catalysts of the present invention refer to the use of at least two different catalysts in different zones of a hydrogenation reactor. To segregate and control each zone, the first and second zones may be in separate beds, vessels or reactors. When segregation is not necessary, the first and second zones may be in the same bed, vessel or reactor. There are several configurations of the zones embodied by the present invention. It should be understood to those skilled in the art that the configurations of the zone are not limited and may be configured in a manner to achieve improved productivity and performance.

In one embodiment, the reactor may comprise a stacked-bed reactor that contains multiple beds in a single vessel. Stacked-bed reactors are typically used when no separation of the effluent between beds is needed and no further reactants are fed to the successive beds. In other embodiments, the reactor may comprise a multiple bed reactor having multiple beds in separate vessels. There also may be multiple reactors each containing catalyst beds having either the first or second zones. Multiple beds or multiple reactors may be used for impurity removal, heating/cooling, or additional feeds, i.e. recycles or fresh reactants, are used between the successive beds or reactors. In addition, separate vessels or multiple reactors may be suitable when there are different reaction conditions for each catalyst or separate reactant feeds. Multiple beds or multiple reactors may allow one to change or replace one bed without a complete loss of production.

The order of the zones may vary when the first and second zones are in series. This allows the reactants to passed to the first zone to form an effluent and the effluent is passed to the second zone to produce ethanol. The effluent contains a crude product of ethanol, unreacted acetic acid, excess hydrogen and other impurities. Additional reactants, in particular hydrogen, may be added to second zone. As indicated herein the first zone designates the zone that contains the mixed oxide catalyst, but it is not required to be the initial zone in a series of beds. Thus, in other embodiments, the reactants are passed to the second zone to form an effluent and the effluent is passed to the first zone containing the mixed oxide catalyst to produce ethanol. Advantageously, mixed oxide catalysts of the present invention in the first zone may have bifunctionality and are more suitable to being used in a subsequent or final catalyst bed in the series. Additional reactants, in particular hydrogen, may be added to first zone. Although the first and second zones may be arranged in parallel, this is not a preferred configuration to take advantage of both catalysts on one pass of reactants.

The zonal catalysts of the present invention are used in a heterogeneous reaction, and may be in a pellet form that is suitable to being distributed throughout the reactor. In some embodiments, the first and second zone are distributed throughout the reactor, and more preferably within one bed of the reactor. This configuration may be suitable when the reaction conditions are similar for each type of zonal catalyst. In one embodiment, the first and second zones are interspersed throughout the reactor so that first and second zones are scattered in a non-uniform manner. In other embodiments, there may be a gradient concentration distribution. For example, near the top of the bed the concentration of the first catalyst may be high and decrease steadily down through the bed. Likewise the second catalyst may be in a high concentration near the bottom of the bed and steadily decrease in concentration up through the bed. The interface between the gradients may be separated by a catalyst support in the bed.

The size of each zone may vary as needed to achieve the desired performance. In one embodiment, the initial zone in the series may have a greater bed volume than the other beds, and, preferably, the bed volume of the first zone may be at least 1.5 times larger than the other beds, and more preferably at least 2 times larger or at least 2.5 times larger. Without being bound by theory, a larger initial zone may ensure that acetic acid is consumed in a sufficient manner. In one embodiment, the weight ratio of the first catalyst to second catalyst is from 20:80 to 80:20, e.g., more preferable from 40:60 to 60:40.

Mixed Oxide Catalysts

For purposes of the present invention, the first catalyst, or mixed oxide catalyst, comprises a mixed oxide comprising tin and at least one of cobalt or nickel. The mixed oxide catalyst may also comprise a binder. A mixed oxide refers to an oxide having cations of more than one chemical element. For purposes of the present invention, mixed oxides include the reduced metals of the mixed oxide. Without being bound by theory a mixed oxide catalyst may be bifunctional, meaning that is able to convert two different reactants, such as acetic acid and ethyl acetate. Thus, mixed oxide catalyst may be particularly advantageous in zones that receive greater mixtures of reactants, and in particular ethyl acetate, either from recycles or from effluent of prior beds.

There several mixed oxide catalysts suitable for used in the present invention. In general the mixed oxide catalysts share the following commonalities. Each mixed oxide catalyst comprises a binder. The binder may be an inert material which is used to enhance the crush strength of the mixed oxide catalyst. The binder is preferably stable under the hydrogenation conditions. Suitable inert materials comprise silica, aluminum oxide, and titania. The binder may be present in an amount from 5 to 40 wt. %, e.g. from 10 to 35 wt. % or from 10 to 20 wt. %, based on the total weight of the mixed oxide catalyst. Unless otherwise stated, all ranges disclosed herein include both endpoints and all numbers between the endpoints.

Regardless of the type of mixed oxide, the loading of the mixed oxide may range from 40 to 90 wt. %, based on the total weight of the mixed oxide catalyst, and more preferably from 60 to 90 wt. %, or more preferably from 70 to 85 wt. %. The combined total metal loading of the tin and at least one of cobalt or nickel, may be at least 40 wt. %, based on the total weight of the catalyst, e.g., more preferably at least 45 wt. % or at least 50 wt. %. Lower loadings of cobalt and tin in the mixed oxide catalyst of less than 20 wt. % are to be avoided since this decreases the conversion of acetic acid and/or selectivity to ethanol.

The mixed oxide may be substantially free of non-precious promoter metals, such as, silver, zinc, zirconium, cadmium, copper, manganese, or molybdenum, including combinations thereof "Substantially free" means that the mixed oxide catalyst does not contain promoter metal(s) beyond trace amounts of less than 0.0001 wt. % of the total metal content of the catalyst. When the mixed oxide is substantially free of these non-precious promoter metals, it is preferred that the binder and thus the catalyst itself are also substantially free of these non-precious promoter metals. Some mixed oxide catalysts may be substantially free of precious promoter metals, as described further herein.

The surface area of the mixed oxide catalyst may be from 100 to 250 m$^2$/g, e.g., from 150 to 180 m$^2$/g. Pore volumes are between 0.18 and 0.35 mL/g, with average pore diameters from 6 to 8 nm. The morphology of the catalyst may be pellets, extrudates, spheres, spray dried microspheres, rings, pentarings, trilobes, quadrilobes, multi-lobal shapes, or flakes. The shape of the mixed oxide catalyst may be determined by hydrogen process conditions to provide a shape that can withstand pressure drops in the first zone.

The mixed oxide catalysts of the present invention have an on-stream stability for at least 200 hours at constant reaction conditions. Stability refers to a catalyst that has a change of less than 2% in conversion and less than 2% selectivity to ethanol, after initial break-in. In addition, stability may also refer to a mixed oxide catalyst that does not demonstrate increase by-product formation while on-stream. This greatly improves the industrial usefulness of a mixed oxide catalyst for continuous production with multiple zones. Also, this reduces the need to replace the mixed oxide catalyst and reduces reactor down time for continuous processes.

For mixed oxides with cobalt and tin, and without being bound by theory, cobalt and tin may be predominately present on the catalyst as a mixed oxide, such as cobalt(II)-stannate. However, the catalyst may contain some discrete regions of cobalt oxide and tin oxide. In addition, metallic cobalt or tin, i.e. as reduced metals, may also be present on the mixed oxide catalyst. The mixed oxide, and the catalyst itself, is preferably anhydrous. The total cobalt loading of the mixed oxide catalyst may be from 10 to 60 wt. %, e.g., from 25 to 45 wt. % or from 30 to 40 wt. %, based on the total metal content of the catalyst. The total tin loading of the mixed oxide catalyst may be from 10 to 60 wt. %, e.g., from 35 to 55 wt. %, based on the total metal content of the catalyst. A molar ratio of cobalt to tin that is from 2:1 to 0.75:1 may be employed, e.g., from 1.5:1 to 1:1 or from 1.4:1 to 1.1:1. A molar excess of cobalt may improve the selectivity to ethanol.

In embodiments that have a mixed oxide comprising cobalt and tin, the mixed oxide may further comprise nickel. The total nickel loading of the mixed oxide catalyst may be from 0.5 to 40 wt. %, e.g., from 1 to 20 wt. %, based on the total metal content of the mixed oxide catalyst. Without being bound by theory, nickel may improve the activity of the mixed oxide catalysts to convert acetic acid. In addition, nickel may be useful for converting other oxygenates in the feed, such as ethyl acetate. The other oxygenates may also be formed in the reactor as by-products.

The further differences of the mixed oxide catalysts are based on mixed oxide, the presence of precious promoter metals or the absence of such precious promoter metals, and the use of a bismuth promoter. In some embodiments, the mixed oxide may comprise cobalt and tin, and in other embodiments the mixed oxide may comprise nickel and tin. Precious promoter metals include rhenium, ruthenium, rhodium, palladium, osmium, iridium, platinum, and combinations thereof. The precious promoter metals tend to be expensive and it is desirable to lower the loadings of these metals. In one embodiment, the mixed oxide catalyst may be substantially free of precious promoter metals, while in other embodiments, the mixed oxide catalyst may contain small amounts of the precious promoter metal.

The following exemplary mixed oxide catalysts are particular advantageous for converting acetic acid, in addition to ethyl acetate, to ethanol.

The first exemplary mixed oxide catalyst of the present invention comprises a binder, as discussed above, and a mixed oxide comprising cobalt and tin. The first exemplary mixed oxide catalyst is substantially free of rhenium, ruthenium, rhodium, palladium, osmium, iridium, platinum, and combinations thereof. To reduce the cost, the first exemplary mixed oxide catalyst of the present invention is preferably substantially free of such precious metals, but still demonstrates a high stability with high conversion of acetic acid and selectivity to ethanol. The first exemplary mixed oxide catalyst is approximately 80 wt. % of a cobalt-tin oxide and approximately 20 wt. % of a silica binder.

The second exemplary mixed oxide catalyst of the present invention comprises a binder, as discussed above, and a mixed oxide comprising a promoter metal, cobalt, and tin. Unlike the first exemplary mixed oxide catalyst, the second exemplary mixed oxide catalyst comprises a promoter metal that is selected from the group consisting of rhenium, ruthenium, rhodium, palladium, osmium, iridium, platinum, and combinations thereof. Preferably, the promoter metal is rhenium, ruthenium, or combinations thereof. In one embodiment, the promoter metal is present in an amount from 0.01 to 10 wt. %, based on the total weight of the catalyst. More preferably the promoter metal is present in an amount from 0.05 to 3 wt. %, based on the total weight of the second exemplary mixed oxide catalyst. Without being bound by theory, the promoter preferably as a potential activity on acid hydrogenation and ethyl acetate hydrolysis. The second exemplary mixed oxide catalyst is approximately 80 wt. % of a cobalt-tin oxide, approximately 1 wt. % ruthenium, and approximately 19 wt. % of a silica binder.

The third exemplary mixed oxide catalyst of the present invention comprises a binder, as discussed above, bismuth, and a mixed oxide comprises cobalt, and tin. Bismuth may be present as a promoter metal. Similar to the first exemplary mixed oxide catalyst, the third exemplary mixed oxide catalyst is also substantially free of rhenium, ruthenium, rhodium, palladium, osmium, iridium, platinum, and combinations thereof. The total bismuth loading of the catalyst may be from 0.1 to 10 wt. % of the total weight of the catalyst, e.g., from 0.25 to 3 wt. %. The third exemplary mixed oxide catalyst is approximately 80 wt. % of a cobalt-tin oxide, approximately 1 wt. % bismuth, and approximately 19 wt. % of a silica binder.

The fourth exemplary mixed oxide catalyst of the present invention comprises a binder, as discussed above, ruthenium, bismuth, and a mixed oxide comprises cobalt, and tin. Ruthenium and bismuth may be present as promoter metals. The fourth exemplary mixed oxide catalyst is approximately 80 wt. % of a cobalt-tin oxide, approximately 0.5 wt. % ruthenium, approximately 1 wt. % bismuth, and approximately 18.5 wt. % of a silica binder.

The fifth exemplary mixed oxide catalyst of the present invention comprises a binder, as discussed above, and a mixed oxide comprising nickel and tin. The mixed oxide of nickel and tin may contain one or more of the precious promoter metals described herein. The total nickel loading of the catalyst may be from 25 to 80 wt. %, e.g., from 40 to 70 wt. %, based on the total metal content of the catalyst. The total tin loading of the catalyst may be from 30 to 70 wt. %, e.g., from 40 to 60 wt. %, based on the total metal content of the catalyst. Lower loadings of nickel and tin of less than 20 wt. % are to be avoided since this decreases the conversion of acetic acid and/or selectivity to ethanol. The fifth exemplary mixed oxide catalyst is approximately 80 wt. % of a nickel-tin oxide and approximately 20 wt. % of a silica binder.

In some embodiments, the second catalyst may also comprise a mixed oxide catalyst that is different from the mixed oxide catalyst in the first zone. For example, the mixed oxide catalyst in the first zone may comprise cobalt and tin and is substantially free of rhenium, ruthenium, rhodium, palladium, osmium, iridium, platinum, and combinations thereof may be combined with another mixed oxide in the second zone that may comprise cobalt and tin and contains small amounts of rhenium, ruthenium, rhodium, palladium, osmium, iridium, platinum, and combinations thereof. This may further reduce the amount of these metals and further reduce the cost of the zonal catalysts.

Second Catalyst: Supported Group VIII Hydrogenation Catalyst

In one embodiment, the second zone may comprise a supported Group VIII hydrogenation catalyst. Suitable Group VIII hydrogenation catalyst are described in U.S. Pat. Nos. 7,608,744; 7,863,489; 8,080,694; 8,309,772; 8,338,650; 8,350,886; 8,471,075; 8,501,652; 8,865,609; 8,975,200; and US Pub. No. 2013/0178663; the entire contents and disclosure of which are hereby incorporated by reference. More suitably for the second zone of the present invention, the supported Group VIII hydrogenation catalyst comprises:

a) a support material selected from the group consisting of silica, silica/alumina, calcium metasilicate, pyrogenic silica, high purity silica, carbon, activated carbon, alumina, titiana, zirconia, graphite, zeolites, and mixtures thereof;

b) a support modifier;

c) a Group VIII metal selected from the group consisting of cobalt, rhodium, ruthenium, platinum, palladium, osmium, and iridium; and d) an active metal selected from the group consisting of rhenium, copper, iron, cobalt, vanadium, nickel, titanium, zinc, chromium, molybdenum, tungsten, tin, lanthanum, cerium, manganese, and combinations thereof.

As will be appreciated by those of ordinary skill in the art, support materials may be selected such that the supported Group VIII hydrogenation catalyst is suitably active, selective and robust under the process conditions employed for the formation of ethanol. Suitable support materials may include, for example, stable metal oxide-based supports or ceramic-based supports. Preferred support materials include silica, silica/alumina, pyrogenic silica, high purity silica, or a carbon support (e.g., carbon black or activated carbon) and mixtures thereof. Other supports may be used in some embodiments of the present invention, including without limitation, iron oxide, alumina, titania, zirconia, magnesium oxide, carbon, graphite, high surface area graphitized carbon, activated carbons, and mixtures thereof. In preferred embodiments, the support material is present in an amount from 25 wt. % to 99 wt. %, e.g., from 30 wt. % to 98 wt. % or from 35 wt. % to 95 wt. %, based on total weight of the supported Group VIII hydrogenation catalyst.

In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the support material. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. Larger amounts of acidic impurities, such as aluminum, can be tolerated so long as they are substantially counter-balanced by an appropriate amount of a support modifier as described herein.

The surface area of the silicaceous support material, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In one aspect, catalysts having a trilobe or quadrilobe shape may have an increased surface area. In terms of ranges, the silicaceous support material preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting supported Group VIII hydrogenation catalyst, may vary widely. In some exemplary embodiments, the morphology of the support material may be pellets, extrudates, spheres, spray dried microspheres, rings, pentarings, trilobes, quadrilobes, multi-lobal shapes, or flakes. In one aspect, the support material may have a shape having an increase surface area relative to the length, such as a trilobe or quadrilobe shape. Preferably, the silicaceous support material has a morphology that allows for a packing density of from 0.1 to 1.0 $g/cm^3$, e.g., from 0.2 to 0.9 $g/cm^3$ or from 0.5 to 0.8 $g/cm^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the two or more metal(s) that are disposed on or within the support material and support modifier are generally very small in size, they should not substantially impact the size of the overall catalyst particles. Thus, the above particle sizes generally apply to both the size of the support materials and the final catalyst particles.

The supported Group VIII hydrogenation catalyst may also comprise a support modifier. Support modifiers may adjust the acidity of the support material. For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of support modifiers that adjusts the acidity of the support to make the support less acidic or more basic favors formation of ethanol over other hydrogenation products.

In one embodiment, the support modifiers are present in an amount from 0.1 wt. % to 50 wt. %, e.g., from 0.2 wt. % to 25 wt. %, from 0.5 wt. % to 20 wt. %, or from 1 wt. % to 15 wt. %, based on the total weight of the supported Group VIII hydrogenation catalyst. When the support modifier comprises tungsten, molybdenum, and vanadium, the support modifier may be present in an amount from 0.1 to 40 wt. %, e.g., from 0.1 to 30 wt. % or from 0.1 to 20 wt. %, based on the total weight of the supported Group VIII hydrogenation catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $WO_3$, $MoO_3$, $Cr_2O_3$, $V_2O_5$, $MnO_2$, and $Bi_2O_3$. Preferred acidic support modifiers include those selected from the group consisting of $WO_3$, $MoO_3$, and $V_2O_5$. In other embodiments that use more acidic modifiers, the acidic modifier may be preferably selected from the group consisting of $TiO_2$, $ZrO_2$, $Nb_2O_5$, $Ta_2O_5$, and $Al_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is calcium silicate, and even more preferably calcium metasilicate ($CaSiO_3$). If the basic support modifier comprises calcium metasilicate, it is preferred that at least a portion of the calcium metasilicate is in crystalline form.

In other embodiments, the support modifier may comprise an active metal(s). Preferably, the active metals that are part of the support modifier may comprise cobalt, tin, and mixture thereof. Without being bound by theory, the active metals, when existing as part of the support modifier, may disperse the other support modifier metal or oxide thereof, e.g., calcium, molybdenum or tungsten, on the support material. An active metal is part of the support modifier when it is impregnated and calcined on the support material prior to the impregnation or introduction of the Group VIII metal to the modified support, a combination of the support material and support modifier. Preferred support modifiers may comprise the following combinations of active metals and support modifiers: tungsten and cobalt; tungsten, cobalt and tin; or calcium and cobalt.

In summary, the preferred support modifier may comprise one or more of the following groups: a) calcium, magnesium, or potassium; b) tungsten, molybdenum, or vanadium; c) cobalt or tin.

As indicated above the Group VIII metal for the supported Group VIII hydrogenation catalyst is selected from the group consisting of cobalt, rhodium, ruthenium, platinum, palladium, osmium, and iridium. More preferably the Group VIII metal is platinum or palladium.

In addition to the Group VIII metal, the supported Group VIII hydrogenation catalyst may further comprise an active metal. The active metal may be selected from the group consisting of rhenium, copper, iron, cobalt, vanadium, nickel, titanium, zinc, chromium, molybdenum, tungsten, tin, lanthanum, cerium, manganese, and combinations thereof. More preferably, the active metal is cobalt, vanadium, nickel, titanium, zinc, chromium, molybdenum, tungsten, tin, and combinations thereof. In particular, active metals that use combinations of cobalt and tin are preferred. Further, it should be understood that use of the term "active metal" to refer to some metals in the catalysts of the invention is not meant to suggest that the Group VIII metal that is also included is not catalytically active.

In one embodiment, the total loading of the Group VIII metal and the one or more active metals is from 0.01 to 25 wt. %, e.g., from 0.5 to 15 wt. %, or from 1.0 to 10 wt. %. Thus, unlike the mixed oxide catalyst in the first zone, the metal loading of the supported Group VIII hydrogenation catalyst is lower. The Group VIII metal may be present in an amount from 0.05 to 20 wt. %, e.g. from 0.1 to 10 wt. %, or from 0.5 to 5 wt. %. The active metal may be present in an amount from 0.1 to 20 wt. %, e.g., from 0.1 to 10 wt. %, or from 0.1 to 5 wt. %.

Preferred combinations of Group VIII metals and active metal include platinum/tin, platinum/iron, platinum/rhenium, platinum/cobalt, platinum/nickel, palladium/tin, palladium/rhenium, palladium/cobalt, palladium/copper, palladium/nickel, ruthenium/cobalt, ruthenium/rhenium, ruthenium/iron, rhodium/iron, rhodium/cobalt, rhodium/nickel and rhodium/tin. When two or more active metals are used, preferred combinations include palladium/rhenium/tin, palladium/rhenium/cobalt, palladium/rhenium/nickel, palladium/cobalt/tin, platinum/tin/molybdenum, platinum/tin/iron, platinum/cobalt/tin, platinum/tin/copper, platinum/tin/chromium, platinum/tin/zinc, platinum/tin/nickel, rhodium/nickel/tin, rhodium/cobalt/tin and rhodium/iron/tin.

Exemplary supported Group VIII hydrogenation catalyst for the second zone may comprise one or more the following catalysts. One exemplary catalyst comprises 0.1 to 3 wt. % platinum and 0.5 to 10 wt. % tin on a silica support having, as the support modifier, from 5 to 20 wt. % calcium metasilicate. Another exemplary catalyst comprises 0.1 to 3 wt. % platinum and 0.5 to 10 wt. % tin on a silica support having, as the support modifier, from 5 to 20 wt. % calcium metasilicate and from 0.5 to 10 wt. % cobalt. Another exemplary catalyst comprises 0.1 to 3 wt. % platinum, 0.5 to 10 wt. % tin, and 0.5 to 10 wt. % cobalt on a silica support having, as the support modifier, from 5 to 20 wt. % tungsten. Another exemplary catalyst comprises 0.1 to 3 wt. % platinum and 0.5 to 10 wt. % tin on a silica support having, as the support modifier, from 5 to 20 wt. % tungsten, and 0.5 to 10 wt. % cobalt. Another exemplary catalyst comprises 0.1 to 3 wt. % platinum, 0.5 to 10 wt. % tin, and 0.5 to 10 wt. % cobalt on a silica support having, as the support modifier, from 5 to 20 wt. % tungsten, 0.5 to 10 wt. % tin, and 0.5 to 10 wt. % cobalt.

Second Catalyst: Copper-Based Catalyst

In one embodiment, the second zone may comprise a copper-based catalyst. A copper-based catalyst may comprise zinc, aluminum, chromium, cobalt, or oxides thereof. A copper-zinc or copper-chromium catalyst may particular preferred. Copper may be present in an amount from 35 to 70 wt. % and more preferably 40 to 65 wt. %. Zinc or chromium may be present in an amount from 15 to 40 wt. % and more preferably 20 to 30 wt. %. A copper-based catalyst is particular suited for converting reactants that have more ethyl acetate and can be advantageously be used to convert ethyl acetate that may be formed as a byproduct by other catalysts in other zones. Also, copper-based catalysts are generally at a disadvantage due to long-term catalyst stability. Using a zonal catalysts that comprises a mixed oxide catalyst and a copper-based catalyst may help to alleviate the long-term catalyst stability issues with copper-based catalysts.

Exemplary Zonal Catalysts

As indicated herein there are several combinations of zonal catalysts that are suitable for achieving improved hydrogenation performance. Table 1 indicates several non-limiting zonal catalysts that are in a series of beds or reactors and it indicates that preferred zone for feeding reactants.

TABLE 1

| # | First Zone | Second Zone | Reactants Feed |
|---|---|---|---|
| 1 | CoSnO(80)—SiO$_2$ | Pt(1.1)Sn(1.6)—SiO$_2$Ca$_2$O$_3$(6) | Second |
| 2 | CoSnO(80)Ru(1)—SiO$_2$ | Pt(1.1)Sn(1.6)—SiO$_2$Ca$_2$O$_3$(6) | Second |
| 3 | CoSnO(80)Ru(0.5)Bi(0.5)—SiO$_2$ | Pt(1.1)Sn(1.6)—SiO$_2$Ca$_2$O$_3$(6) | Second |
| 4 | CoSnO(80)Bi(1)—SiO$_2$ | Pt(1.1)Sn(1.6)—SiO$_2$Ca$_2$O$_3$(6) | Second |
| 5 | NiSnO(80)—SiO$_2$ | Pt(1.1)Sn(1.6)—SiO$_2$Ca$_2$O$_3$(6) | Second |
| 6 | CoSnO(80)—SiO$_2$ | Pt(0.5)Sn(0.6)—SiO$_2$Ca$_2$O$_3$(5.6)Co$_3$O$_4$(6.7) | First or Second |
| 7 | CoSnO(80)Ru(1)—SiO$_2$ | Pt(0.5)Sn(0.6)—SiO$_2$Ca$_2$O$_3$(5.6)Co$_3$O$_4$(6.7) | First or Second |
| 8 | CoSnO(80)Ru(0.5)Bi(0.5)—SiO$_2$ | Pt(0.5)Sn(0.6)—SiO$_2$Ca$_2$O$_3$(5.6)Co$_3$O$_4$(6.7) | First or Second |
| 9 | CoSnO(80)Bi(1)—SiO$_2$ | Pt(0.5)Sn(0.6)—SiO$_2$Ca$_2$O$_3$(5.6)Co$_3$O$_4$(6.7) | First or Second |
| 10 | NiSnO(80)—SiO$_2$ | Pt(0.5)Sn(0.6)—SiO$_2$Ca$_2$O$_3$(5.6)Co$_3$O$_4$(6.7) | Second |
| 11 | CoSnO(80)—SiO$_2$ | Pt(1)Co(4.8)Sn(4.1)—SiO$_2$WO$_3$(16) | First or Second |
| 12 | CoSnO(80)Ru(1)—SiO$_2$ | Pt(1)Co(4.8)Sn(4.1)—SiO$_2$WO$_3$(16) | First or Second |
| 13 | CoSnO(80)Ru(0.5)Bi(0.5)—SiO$_2$ | Pt(1)Co(4.8)Sn(4.1)—SiO$_2$WO$_3$(16) | First or Second |
| 14 | CoSnO(80)Bi(1)—SiO$_2$ | Pt(1)Co(4.8)Sn(4.1)—SiO$_2$WO$_3$(16) | First or Second |
| 15 | NiSnO(80)—SiO$_2$ | Pt(1)Co(4.8)Sn(4.1)—SiO$_2$WO$_3$(16) | Second |
| 16 | CoSnO(80)—SiO$_2$ | Pt(1.09)Co(3.75)Sn(3.25)—SiO$_2$Co(3.75)Sn(3.25)WO$_3$(16) | First or Second |
| 17 | CoSnO(80)Ru(1)—SiO$_2$ | Pt(1.09)Co(3.75)Sn(3.25)—SiO$_2$Co(3.75)Sn(3.25)WO$_3$(16) | First or Second |
| 18 | CoSnO(80)Ru(0.5)Bi(0.5)—SiO$_2$ | Pt(1.09)Co(3.75)Sn(3.25)—SiO$_2$Co(3.75)Sn(3.25)WO$_3$(16) | First or Second |
| 19 | CoSnO(80)Bi(1)—SiO$_2$ | Pt(1.09)Co(3.75)Sn(3.25)—SiO$_2$Co(3.75)Sn(3.25)WO$_3$(16) | First or Second |

TABLE 1-continued

| # | First Zone | Second Zone | Reactants Feed |
|---|---|---|---|
| 20 | NiSnO(80)—SiO$_2$ | Pt(1.09)Co(3.75)Sn(3.25)—SiO$_2$Co(3.75)Sn(3.25)WO$_3$(16) | Second |
| 21 | CoSnO(80)—SiO$_2$ | Pt(1.09)Sn(1.2)—SiO$_2$Co(7.5)WO$_3$(16) | First or Second |
| 22 | CoSnO(80)Ru(1)—SiO$_2$ | Pt(1.09)Sn(1.2)—SiO$_2$Co(7.5)WO$_3$(16) | First or Second |
| 23 | CoSnO(80)Ru(0.5)Bi(0.5)—SiO$_2$ | Pt(1.09)Sn(1.2)—SiO$_2$Co(7.5)WO$_3$(16) | First or Second |
| 24 | CoSnO(80)Bi(1)—SiO$_2$ | Pt(1.09)Sn(1.2)—SiO$_2$Co(7.5)WO$_3$(16) | First or Second |
| 25 | NiSnO(80)—SiO$_2$ | Pt(1.09)Sn(1.2)—SiO$_2$Co(7.5)WO$_3$(16) | Second |
| 26 | CoSnO(80)—SiO$_2$ | Cu(65)Zn(25)—Al$_2$O$_3$ | First |
| 27 | CoSnO(80)Ru(1)—SiO$_2$ | Cu(65)Zn(25)—Al$_2$O$_3$ | First |
| 28 | CoSnO(80)Ru(0.5)Bi(0.5)—SiO$_2$ | Cu(65)Zn(25)—Al$_2$O$_3$ | First |
| 29 | CoSnO(80)Bi(1)—SiO$_2$ | Cu(65)Zn(25)—Al$_2$O$_3$ | First |
| 30 | NiSnO(80)—SiO$_2$ | Cu(65)Zn(25)—Al$_2$O$_3$ | First |
| 31 | CoSnO(80)—SiO$_2$ | CoSnO(80)Ru(1)—SiO$_2$ | First or Second |
| 32 | CoSnO(80)—SiO$_2$ | CoSnO(80)Ru(0.5)Bi(0.5)—SiO$_2$ | First or Second |
| 33 | CoSnO(80)—SiO$_2$ | CoSnO(80)Bi(1)—SiO$_2$ | First or Second |
| 34 | CoSnO(80)—SiO$_2$ | NiSnO(80)—SiO$_2$ | First |
| 35 | CoSnO(80)Ru(1)—SiO$_2$ | CoSnO(80)Ru(0.5)Bi(0.5)—SiO$_2$ | First or Second |
| 36 | CoSnO(80)Ru(1)—SiO$_2$ | CoSnO(80)Bi(1)—SiO$_2$ | First or Second |
| 37 | CoSnO(80)Ru(1)—SiO$_2$ | NiSnO(80)—SiO$_2$ | First |
| 38 | CoSnO(80)Ru(0.5)Bi(0.5)—SiO$_2$ | CoSnO(80)Bi(1)—SiO$_2$ | First or Second |
| 39 | CoSnO(80)Ru(0.5)Bi(0.5)—SiO$_2$ | NiSnO(80)—SiO$_2$ | First |
| 40 | CoSnO(80)Bi(1)—SiO$_2$ | NiSnO(80)—SiO$_2$ | First |

The catalysts shown in Table 1 are reported using the following conventions. First, the number in parenthesis indicates the weight percent of the component prior to the parenthesis. Also these numbers are approximate weight percent. For example, CoSnO(80) means approximately 80 wt. %, based on the total weight of the catalyst, is a mixed oxide of Co and Sn. Second, the weight percent for the binders of the mixed oxide catalysts and support material in the support Group VIII hydrogenation catalysts are not provided and assumed to the balance of the catalyst. Third, for support Group VIII hydrogenation catalysts the components after the support material, i.e. SiO$_2$, are the support modifiers.

Hydrogenation

Hydrogenation generally involves converting acetic acid, and other reactants, to produce ethanol. The reactants are fed to either the first zone or second zone, depending on the configuration as described above. The reactants, i.e. feed stream, to the hydrogenation process preferably comprises acetic acid and hydrogen. In some embodiments, pure acetic acid may be used as the feed. In other embodiments, the feed stream may contain some other oxygenates, such as ethyl acetate, acetaldehyde, or diethyl acetal, or higher acids, such as propanoic acid or butanoic acid. Minor amounts of ethanol may also be present in the feed stream. For purposes of characterizing the feed stream the weight percent excludes hydrogen. In one embodiment, the feed stream may comprise from 50 to 95 wt. % acetic acid, and from 5 to 50 wt. % oxygenates. More preferably, the feed stream may comprise from 60 to 95 wt. % acetic acid and from 5 to 40 wt. % ethyl acetate. The other oxygenates may originate from recycle streams that are fed to the hydrogenation reactor. In other embodiments, the feed stream may comprise from 0 to 15 wt. % water, e.g., from 0.1 to 10 wt. % water. An exemplary feed stream, e.g., a mixed feed stream, may comprise from 50 to 95 wt. % acetic acid, from 5 to 50 wt. % ethyl acetate, from 0.01 to 10 wt. % acetaldehyde, from 0.01 to 10 wt. % ethanol, and from 0.01 to 10 wt. % diethyl acetal.

The process of hydrogenating acetic acid to form ethanol using zonal catalysts according to one embodiment of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. Typically, the zonal catalyst are employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the zonal catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions in both the first and second zones. The reaction temperature may range from 200° C. to 350° C., e.g., from 200° C. to 325° C., from 225° C. to 300° C., or from 250° C. to 300° C. The pressure may range from 101 kPa to 3000 kPa (about 1 to 30 atmospheres), e.g., from 101 kPa to 2700 kPa, or from 101 kPa to 2300 kPa. The reactants may be fed to the reactor at a gas hourly space velocities (GHSV) of greater than 500 hr$^{-1}$, e.g., greater than 1000 hr$^{-1}$, greater than 2500 hr$^{-1}$ and even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 8000 hr$^{-1}$.

In some embodiments, when the second zone comprises a copper-based catalyst, the reaction temperature may be from 125° C. to 350° C., e.g., from 180° C. to 345° C., from 225° C. to 310° C., or from 290° C. to 305° C. The pressure may range from 700 to 8,500 kPa, e.g., from 1,500 to 7,000 kPa, or from 2,000 to 6,500 kPa. The reactants may be fed to the reactor at a gas hourly space velocities (GHSV) of greater than 500 hr$^{-1}$, e.g., greater than 1000 hr$^{-1}$, greater than 2500 hr$^{-1}$ and even greater than 5000 hr$^{-1}$.

Although the reaction consumes two moles of hydrogen per mole of acetic acid to produce one mole of ethanol, the actual molar ratio of hydrogen to acetic acid in the feed stream may vary from 100:1 to 1:100, e.g., from 50:1 to 1:50, from 20:1 to 1:2, or from 12:1 to 1:1. Most preferably, the molar ratio of hydrogen to acetic acid is equal to or greater than 4:1, e.g., greater than 5:1 or greater than 8:1. In some embodiments, when hydrogen is fed to one zone and passed through to the other zone, the hydrogen molar ratio may be larger in the initial zone to ensure sufficient hydrogen for the other zone. In other embodiments, hydrogen may be fed to each zone to maintain sufficient pressure and hydrogen molar ratios.

Contact or residence time can also vary widely, depending upon such variables as amount of acetic acid, catalyst, reactor, temperature and pressure. Typical contact times range from a fraction of a second to more than several hours when a catalyst system other than a fixed bed is used. Preferred contact times, at least for vapor phase reactions, in each zone may range from 0.1 to 100 seconds, e.g., from 0.3 to 80 seconds or from 0.4 to 40 seconds. The contact time in each zone may also vary depending on the size of the zone.

The acetic acid, along with any other reactants, may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using zonal catalysts of the present invention may achieve favorable conversion of acetic acid and favorable selectivity and productivity to ethanol. For purposes of the present invention, the term conversion refers to the amount of acetic acid that is converted to a compound other than acetic acid. Conversion is expressed as a mole percentage based on acetic acid in the feed stream.

The conversion of acetic acid (AcOH) is calculated from gas chromatography (GC) data using the following equation:

$$AcOH\ Conv.\ (\%) = 100 * \frac{\text{mmol AcOH (feed stream)} - \text{mmol AcOH }(GC)}{\text{mmol AcOH (feed stream)}}$$

The first and second catalysts may have different individual conversions, provided that the total conversion of the zonal catalysts is at least 60%, e.g., at least 70% or at least 80%. Mixed oxide catalysts may have conversions that are at least 70%, e.g., at least 80% or at least 90%. This may allow a catalyst with a lower conversion, but high selectivity, to be in one zone and catalysts with a high conversion, such as mixed oxide catalysts, in a subsequent zone in the series. Although catalysts that have high conversions are desirable, such as at least 80% or at least 90%, a low conversion may be acceptable at high selectivity for ethanol.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Selectivity to ethanol (EtOH) is calculated from gas chromatography (GC) data using the following equation:

$$EtOH\ Sel.\ (\%) = 100 * \frac{\text{mmol }EtOH\ (GC)}{\frac{\text{Total mmol C }(GC)}{2} - \text{mmol AcOH (feed stream)}}$$

wherein "Total mmol C (GC)" refers to total mmols of carbon from all of the products analyzed by gas chromatograph.

For purposes of the present invention, the total selectivity to ethanol of the zonal catalysts is at least 80%, e.g., at least 85% or at least 88%. The mixed oxide catalysts of the present invention may have a selectivity to ethanol that is at least 50%, e.g., at least 70% or at least 85%. For both the first and second catalysts, it is also desirable to have low selectivity to undesirable products, such as methane, ethane, and carbon dioxide. The selectivity to these undesirable products is less than 4%, e.g., less than 2% or less than 1%. Preferably, no detectable amounts of these undesirable products are formed during hydrogenation. In several embodiments of the present invention, formation of alkanes from either the first or second catalysts is low, usually under 2%, often under 1%, and in many cases under 0.5% of the acetic acid passed over the catalyst is converted to alkanes, which have little value other than as fuel.

Productivity refers to the grams of a specified product, e.g., ethanol, formed during the hydrogenation based on the kilogram of zonal catalyst, i.e. both first and second catalysts, used per hour. In one embodiment of the present invention, a productivity of at least 200 grams of ethanol per kilogram zonal catalyst per hour, e.g., at least 400 grams of ethanol or least 600 grams of ethanol, is preferred. In terms of ranges, the productivity preferably is from 200 to 4,000 grams of ethanol per kilogram zonal catalyst per hour, e.g., from 400 to 3,500 or from 600 to 3,000.

Ethanol Recovery

The hydrogenation of reactants with the zonal catalysts yields a crude ethanol product according to embodiments of the present invention. The crude ethanol product produced by the hydrogenation process of the present invention, before any subsequent processing, such as purification and separation, typically comprises ethanol, water, and unreacted acetic acid, as shown in Table 2. Without being bound by theory the use of zonal catalysts of the present invention may drive the concentration of acetic acid lower due to increased conversion. The amount of impurities and byproducts such as ethyl acetate, acetaldehyde, diethyl acetal and acetone may vary but may be advantageously lower when using zonal catalysts of the present invention. The others may include alkanes, other ethers, other acids and esters, other alcohols, etc. The alcohols may be n-propanol and iso-propanol. Exemplary crude ethanol compositional ranges, excluding hydrogen and other non-condensable gases, in various embodiments of the invention are provided below in Table 2.

TABLE 2

CRUDE ETHANOL PRODUCT COMPOSITIONS

| Component | Conc. (wt. %) | Conc. (wt. %) | Conc. (wt. %) |
|---|---|---|---|
| Ethanol | 25 to 70 | 30 to 60 | 40 to 55 |
| Acetic Acid | 0 to 30 | 0.05 to 25 | 0.1 to 20 |
| Ethyl Acetate | 0 to 20 | 0.1 to 15 | 1 to 10 |
| Acetaldehyde | 0 to 20 | 0.5 to 10 | 1 to 5 |
| Diethyl Acetal | 0 to 35 | 0.5 to 20 | 1 to 15 |
| Water | 5 to 35 | 5 to 30 | 5 to 25 |
| Acetone | 0 to 10 | 0 to 5 | 0 to 1 |
| Other | 0 to 10 | 0 to 5 | 0 to 1 |

An ethanol product may be recovered from the crude ethanol product produced by the reactor using the zonal catalysts of the present invention using several different techniques, such as distillation columns, adsorption units, membranes, or molecular sieves. For example, multiple columns may be used to remove impurities and concentration ethanol to an industrial grade ethanol or an anhydrous ethanol suitable for fuel applications. Exemplary separation and recovery processes are disclosed in U.S. Pat. Nos. 8,309,773; 8,304,586; and 8,304,587; and U.S. Pub. Nos. 2012/0010438; 2012/0277490; and 2012/0277497, the entire contents and disclosure of which are hereby incorporated by reference.

In one embodiment, the process may comprise hydrogenating an acetic acid feed stream in a reactor in the presence of a first catalyst in a first zone and a second catalyst in a second zone, wherein the first catalyst comprises a mixed oxide comprising tin and at least one of cobalt or nickel, to form a crude ethanol product, separating at least a portion of the crude ethanol product in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, wherein the second column is an extractive distillation column, feeding an extraction agent to the second column, and separating at least a portion of the second residue in a third column into a third distillate comprising ethanol and a third residue comprising water. Water from the third residue may be used as the extraction agent. Also, a fourth column may be used to separate light compounds such as acetaldehyde and acetone from the second distillate to yield an ethyl acetate co-product.

In another embodiment, the process may comprising hydrogenating acetic acid and/or an ester thereof in a reactor in the presence of a first catalyst in a first zone and a second catalyst in a second zone, wherein the first catalyst comprises a mixed oxide comprising tin and at least one of cobalt or nickel, form a crude ethanol product, separating a portion of the crude ethanol product in a first distillation column to yield a first distillate comprising acetaldehyde and ethyl acetate, and a first residue comprising ethanol, acetic acid, ethyl acetate and water, separating a portion of the first residue in a second distillation column to yield a second residue comprising acetic acid and an vapor overhead comprising ethanol, ethyl acetate and water, removing water, using a membrane or pressure swing absorption, from at least a portion of the vapor overhead to yield an ethanol mixture stream having a lower water content than the at least a portion of the vapor overhead, and separating at least a portion of the ethanol mixture stream in a third distillation column to yield a third distillate comprising ethyl acetate and a third residue comprising ethanol and less than 8 wt. % water.

The raw materials used in connection with the process of this invention may be derived from any suitable source including natural gas, petroleum, coal, biomass and so forth. It is well known to produce acetic acid through methanol carbonylation, acetaldehyde oxidation, ethane oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352 the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111, which discloses a process for converting waste biomass through gasification into synthesis gas as well as U.S. Pat. No. 6,685,754, the disclosures of which are incorporated herein by reference.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

In one embodiment, the process may comprise a process for the formation of ethanol comprising, converting a carbon source into acetic acid, and contacting a feed stream containing the acetic acid and hydrogen with of a first catalyst in a first zone and a second catalyst in a second zone, wherein the first catalyst comprises a mixed oxide comprising tin and at least one of cobalt or nickel. In another embodiment, the process may comprise a process for the formation of ethanol comprising converting a carbon source, such as biomass, into a first stream comprising syngas, catalytically converting at least some of the syngas into a second stream comprising methanol, separating some of the syngas into hydrogen and carbon monoxide, catalytically converting at least some of the methanol with some of the carbon monoxide into a third stream comprising acetic acid; and reducing at least some of the acetic acid with some of the hydrogen in the presence of a first catalyst in a first zone and a second catalyst in a second zone, wherein the first catalyst is a mixed oxide catalyst comprising a mixed oxide comprising tin and at least one of cobalt or nickel, into a fourth stream comprising ethanol.

Ethanol, obtained from hydrogenation processes of the present invention, may be used in its own right as a fuel or subsequently converted to ethylene which is an important commodity feedstock as it can be converted to polyethylene, vinyl acetate and/or ethyl acetate or any of a wide variety of other chemical products. Any known dehydration catalyst, such as zeolite catalysts or phosphotungstic acid catalysts, can be employed to dehydrate ethanol to ethylene, as described in copending U.S. Pub. Nos. 2010/0030002 and 2010/0030001 and WO2010146332, the entire contents and disclosures of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol comprising contacting reactants comprising acetic acid and hydrogen in a reactor in the presence of a first catalyst in a first zone and a second catalyst in a second zone,
   wherein the first catalyst comprises a mixed oxide comprising tin and at least one of cobalt or nickel, wherein the mixed oxide comprising tin and at least one of cobalt or nickel is present in an amount from 60 to 90 wt. %, based on the total weight of the first catalyst; and
   wherein the second catalyst is selected from the group consisting of:
      i) a supported Group VIII hydrogenation catalyst;
      ii) a copper-based catalyst; and
      iii) a secondary mixed oxide catalyst, wherein the secondary mixed oxide catalyst is different than the mixed oxide catalyst of the first zone.

2. The process of claim 1, wherein the first zone is a first bed of the reactor.

3. The process of claim 1, wherein the second zone is a second bed of the reactor.

4. The process of claim 1, wherein the first and second zones are distributed throughout a bed of the reactor.

5. The process of claim 4, wherein the first and second zones are interspersed throughout the bed.

6. The process of claim 4, wherein the first and second zones have a gradient distribution in the bed.

7. The process of claim 1, wherein the reactor comprises separate vessels and the first zone and second zones are in the separate vessels.

8. The process of claim 1, wherein the weight ratio of the first catalyst to second catalyst is from 20:80 to 80:20.

9. The process of claim 1, wherein the reactants are passed to the first zone to form an effluent and wherein the effluent is passed to the second zone to produce ethanol.

10. The process of claim 1, wherein the reactants are passed to the second zone to form an effluent and wherein the effluent is passed to the first zone to produce ethanol.

11. The process of claim 1, wherein the first zone and second zone operate independently in a vapor phase at a temperature of 200° C. to 350° C., an absolute pressure of 101 kPa to 3000 kPa, and a hydrogen to acetic acid mole ratio of greater than 4:1.

12. The process of claim 1, wherein the second zone comprises a copper-based catalyst, the second zone operates in a vapor phase at a temperature of 125° C. to 350° C., an absolute pressure of 700 to 8,500 kPa, and a hydrogen to acetic acid mole ratio of greater than 4:1.

13. The process of claim 1, wherein the first catalyst is selected from the group consisting of:
   a) a binder and the mixed oxide comprises cobalt and tin, the catalyst being substantially free of rhenium, ruthenium, rhodium, palladium, osmium, iridium, platinum, and combinations thereof;
   b) a binder and the mixed oxide comprises a promoter metal, cobalt, and tin, wherein the promoter metal is selected from the group consisting of rhenium, ruthenium, rhodium, palladium, osmium, iridium, platinum, and combinations thereof;
   c) a binder, bismuth, and the mixed oxide comprises cobalt, and tin, being substantially free of rhenium, ruthenium, rhodium, palladium, osmium, iridium, platinum, and combinations thereof;
   d) a binder, the mixed oxide comprises cobalt and tin, and at least two promoter metals comprising ruthenium and bismuth; and
   e) a binder and the mixed oxide comprises nickel and tin.

14. The process of claim 13, wherein the combined metal amount of the mixed oxide is at least 40 wt. %, based on the total weight of the first catalyst.

15. The process of claim 13, wherein the binder is selected from the group consisting of silica, aluminum oxide, and titania, and the binder is present in an amount from 5 to 40 wt. %, based on the total weight of the first catalyst.

16. The process of claim 1, wherein the supported Group VIII hydrogenation catalyst comprises:
   a) a support material selected from the group consisting of silica, silica/alumina, calcium metasilicate, pyrogenic silica, high purity silica, carbon, activated carbon, alumina, titiana, zirconia, graphite, zeolites, and mixtures thereof;
   b) a support modifier;
   c) a Group VIII metal selected from the group consisting of cobalt, rhodium, ruthenium, platinum, palladium, osmium, and iridium; and
   d) an active metal selected from the group consisting of rhenium, copper, iron, cobalt, vanadium, nickel, titanium, zinc, chromium, molybdenum, tungsten, tin, lanthanum, cerium, manganese, and combinations thereof.

17. The process of claim 16, wherein the support modifier comprises one or more of the following groups:
   a) calcium, magnesium, or potassium;
   b) tungsten, molybdenum, or vanadium;
   c) cobalt or tin.

18. The process of claim 16, wherein the total loading of the Group VIII metal and the active metal is from 0.01 to 25 wt. %.

19. The process of claim 1, wherein the copper-based catalyst comprises from 35 to 70 wt. % copper, and zinc, chromium, or combinations thereof in an amount from 15 to 40 wt. %.

* * * * *